United States Patent
Gonnelli et al.

(10) Patent No.: US 9,981,083 B2
(45) Date of Patent: *May 29, 2018

(54) FLUID DELIVERY AND MEASUREMENT SYSTEMS AND METHODS

(71) Applicant: Valeritas, Inc., Bridgewater, NJ (US)

(72) Inventors: Robert R. Gonnelli, Mahwah, NJ (US); Steven F. Levesque, North Pembroke, MA (US); David Lipson, North Andover, MA (US); Peter F. Marshall, Lancaster, MA (US)

(73) Assignee: VALERITAS, INC., Wilmington, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/464,570

(22) Filed: Mar. 21, 2017

(65) Prior Publication Data
US 2017/0189610 A1  Jul. 6, 2017

Related U.S. Application Data

(60) Continuation of application No. 14/629,801, filed on Feb. 24, 2015, now Pat. No. 9,636,451, which is a
(Continued)

(51) Int. Cl.
*A61M 5/155* (2006.01)
*A61M 5/145* (2006.01)
(Continued)

(52) U.S. Cl.
CPC ........ *A61M 5/155* (2013.01); *A61M 5/14526* (2013.01); *A61M 5/14593* (2013.01);
(Continued)

(58) Field of Classification Search
CPC .............. A61M 5/155; A61M 5/14526; A61M 5/14593; A61M 5/158; A61M 5/16804; A61M 2005/14204; A61M 2205/8231
USPC ....... 604/131, 141, 145, 153, 136, 138, 142, 604/147, 156, 157, 69, 70, 132, 93.01, 604/110, 134, 135, 139, 140, 148, 181, 604/268, 890.1, 187, 891.1, 209, 192, 604/197, 198, 217; 128/DIG. 12, DIG. 13
See application file for complete search history.

(56) References Cited

U.S. PATENT DOCUMENTS 3,494,358 A   2/1970   Duesterheft et al.
3,894,538 A   7/1975   Richter
(Continued)

FOREIGN PATENT DOCUMENTS

EP   0937475   8/1999
NL   7310455   2/1974
(Continued)

OTHER PUBLICATIONS

Official Action dated Dec. 21, 2010 issued in connection with Russian Application No. 2008143015/14.
(Continued)

*Primary Examiner* — Manuel Mendez
(74) *Attorney, Agent, or Firm* — Morgan, Lewis & Bockius LLP

(57) ABSTRACT

Fluid delivery and measurement systems and methods are disclosed.

16 Claims, 12 Drawing Sheets

Related U.S. Application Data continuation of application No. 13/743,892, filed on Jan. 17, 2013, now Pat. No. 8,992,478, which is a continuation of application No. 12/336,246, filed on Dec. 16, 2008, now Pat. No. 8,858,511, which is a division of application No. 11/219,944, filed on Sep. 6, 2005, now Pat. No. 7,481,792, which is a division of application No. 10/006,526, filed on Nov. 30, 2001, now Pat. No. 6,939,324.

(60) Provisional application No. 60/250,538, filed on Nov. 30, 2000, provisional application No. 60/250,408, filed on Nov. 30, 2000, provisional application No. 60/250,295, filed on Nov. 30, 2000, provisional application No. 60/250,927, filed on Nov. 30, 2000, provisional application No. 60/250,422, filed on Nov. 30, 2000, provisional application No. 60/250,413, filed on Nov. 30, 2000, provisional application No. 60/324,412, filed on Sep. 24, 2001, provisional application No. 60/250,403, filed on Nov. 30, 2000.

(51) Int. Cl.
  *A61M 5/158* (2006.01)
  *A61M 5/168* (2006.01)
  *A61M 5/142* (2006.01)

(52) U.S. Cl.
  CPC ........ *A61M 5/158* (2013.01); *A61M 5/16804* (2013.01); *A61M 2005/14204* (2013.01); *A61M 2205/8231* (2013.01)

(56) References Cited

U.S. PATENT DOCUMENTS

| | | | |
|---|---|---|---|
| 4,340,048 A | 7/1982 | Eckenhoff | |
| 4,417,889 A | 11/1983 | Choi | |
| 4,505,701 A | 3/1985 | Navato | |
| 4,716,343 A | 12/1987 | Lindquist | |
| 4,902,278 A | 2/1990 | Magel et al. | |
| 5,279,607 A | 1/1994 | Schentag et al. | |
| 5,637,099 A | 5/1997 | Durdin et al. | |
| 5,656,032 A | 8/1997 | Kriesel et al. | |
| 5,693,018 A | 12/1997 | Kriesel et al. | |
| 5,735,818 A | 4/1998 | Kriesel et al. | |
| 5,885,250 A | 3/1999 | Kriesel et al. | |
| 5,957,895 A | 9/1999 | Sage et al. | |
| 6,048,328 A | 4/2000 | Haller et al. | |
| 6,068,613 A | 5/2000 | Kriesel et al. | |
| 6,074,369 A | 6/2000 | Sage et al. | |
| 6,186,982 B1 | 2/2001 | Gross et al. | |
| 6,595,956 B1 | 7/2003 | Gross et al. | |
| 6,699,218 B2 | 3/2004 | Flaherty et al. | |
| 6,939,324 B2 * | 9/2005 | Gonnelli | A61M 5/14248 604/142 |
| 7,337,922 B2 | 3/2008 | Rake et al. | |
| 7,481,792 B2 | 1/2009 | Gonnelli et al. | |
| 7,530,968 B2 | 5/2009 | Gonnelli | |
| 7,678,079 B2 | 3/2010 | Shermer et al. | |
| 8,858,511 B2 | 10/2014 | Gonnelli et al. | |
| 2003/0236498 A1 | 12/2003 | Gross et al. | |
| 2004/0064097 A1 | 4/2004 | Peterson | |
| 2005/0033232 A1 | 2/2005 | Kriesel | |
| 2005/0215850 A1 | 9/2005 | Klein et al. | |
| 2006/0264835 A1 | 11/2006 | Nielson et al. | |
| 2009/0240232 A1 | 9/2009 | Gonnelli et al. | |

FOREIGN PATENT DOCUMENTS

| | | |
|---|---|---|
| RU | 2248223 | 3/2005 |
| WO | 199948546 | 9/1999 |
| WO | 00/29049 | 5/2000 |

OTHER PUBLICATIONS

English Translation of First Office Action dated Dec. 27, 2010 issued in connection with Chinese Application No. 20070020245.9.
First EPO Examination Report dated Nov. 2, 2010 issued in connection with European Application No. 01988242.2.
International Search Report and Written Opinion dated Dec. 10, 2010 in connection with International Application No. PCT/US10/52352.
Official Action issued in connection with Russian Application No. 2008143015/14.
English Translation of First Office Action issued in connection with Chinese Application No. 20070020245.9.
First EPO Examination Report issued in connection with European Application No. 01988242.2.
Office Action dated Apr. 23, 2015 with attached Examination Search Report dated Apr. 13, 2015 for Canadian Patent Application No. 2,850,798.
Office Action dated Apr. 21, 2015 with attached Examination Search Report dated Apr. 10, 2015 for Canadian Patent Application No. 2,850,729.
European Examination Report dated Apr. 11, 2017 for European Patent Application No. 12190928.7, 3 pages.

* cited by examiner

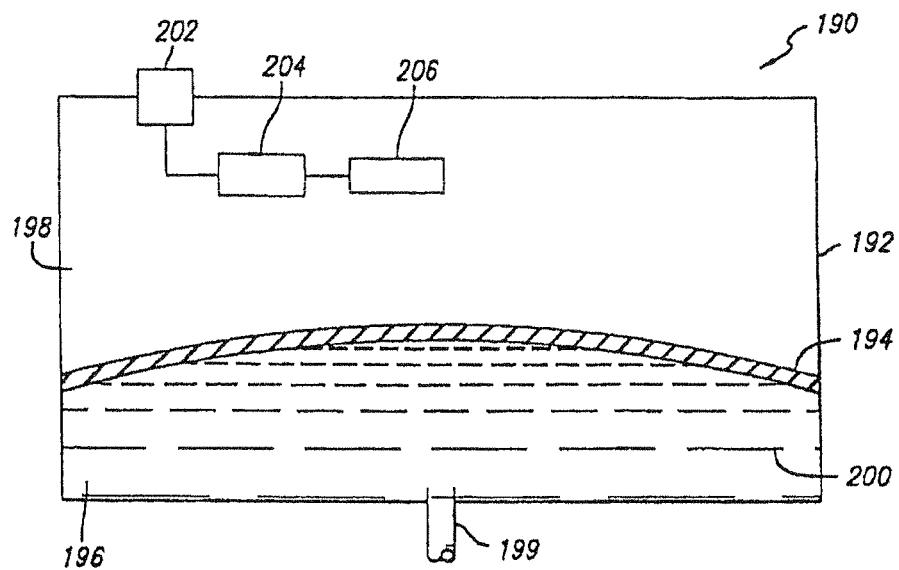
FIG. 9
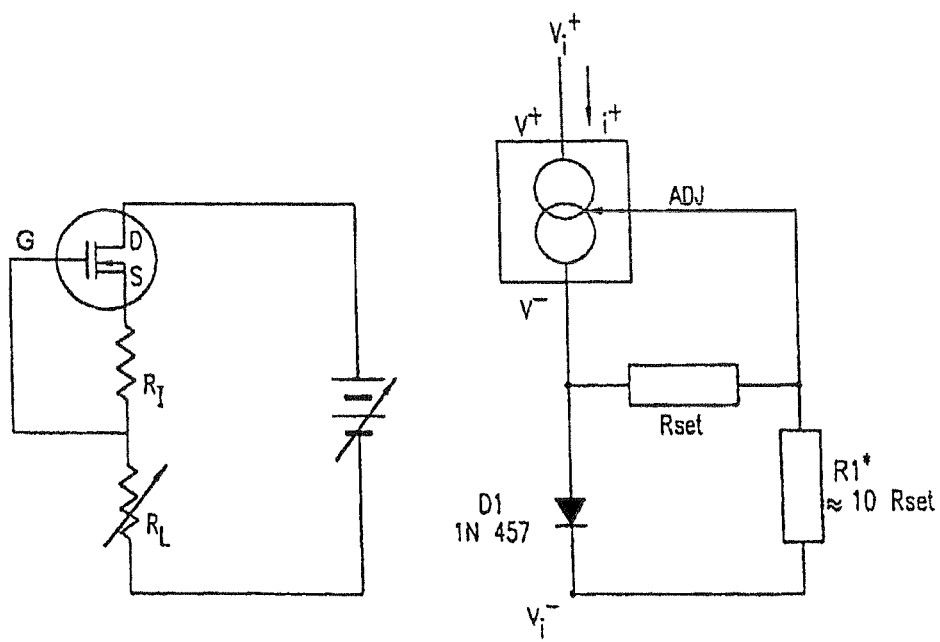
FIG. 10
FIG. 11

FLUID DELIVERY AND MEASUREMENT SYSTEMS AND METHODS

RELATED APPLICATIONS

This application is a continuation of U.S. application Ser. No. 14/629,801 filed on Feb. 24, 2015, which is a continuation of U.S. application Ser. No. 13/743,892 filed on Jan. 17, 2013 (U.S. Pat. No. 8,992,478), which is a continuation of U.S. application Ser. No. 12/336,246 (U.S. Pat. No. 8,858,511) filed on Dec. 16, 2008, which is a divisional of U.S. application Ser. No. 11/219,944 (U.S. Pat. No. 7,481,792), filed on Sep. 6, 2005, which is a divisional of U.S. application Ser. No. 10/006,526 (U.S. Pat. No. 6,939,324), filed on Nov. 30, 2001, which claims the benefit of US. Provisional Patent Application Ser. Nos. 60/250,538, 60/250,408, 60/250,295, 60/250,927, 60/250,422, 60/250,413, and 60/250,403, all filed on Nov. 30, 2000; and of U.S. Provisional Patent Application Ser. No. 60/324,412, filed on Sep. 24, 2001. The entire contents of these applications are hereby incorporated by reference.

FIELD OF THE INVENTION

The invention relates to fluid delivery and measurement systems and methods.

BACKGROUND

Fluid delivery systems can be used to deliver a fluid, such as a pharmacological compound (e.g., a therapeutic agent), from a reservoir to a subject, such as a human. In some embodiments, a fluid delivery system includes a housing containing a deformable membrane and a fluid reservoir. The needle is in fluid communication with the fluid reservoir so that as a force is exerted against the deformable membrane, the fluid can exit the system via the needle. The needle is inserted into a subject (e.g., a human) so that the fluid is injected into the subject as the fluid leaves the system.

SUMMARY

The invention relates to fluid delivery and measurement systems and methods.

In one aspect, the invention features a device that includes a housing and a flexible member within the interior of the housing and mechanically coupled to the housing. The flexible member forms first and second chambers within the interior of the housing. The device further includes a fluid reservoir within the first chamber of the housing and a microprobe extending from the fluid reservoir, through the flexible member and into the second chamber of the housing.

In some embodiments, the microprobe is configured to move substantially freely in three mutually perpendicular directions. In certain embodiments, the microprobe is configured to translate in a first direction and rotate substantially freely in plane perpendicular to the first direction.

In another aspect, the invention features a device that includes a housing and a flexible member within the interior of the housing and mechanically coupled to the housing. The flexible member forms first and second chambers within the interior of the housing. The device also includes a fluid reservoir within the first chamber of the housing, and a flexible tube having a first end and a second end. The first end of the flexible tube is connected to the flexible member and in fluid communication with the fluid reservoir via the flexible member. The device also includes a microprobe connected to the second end of the flexible tube. The microprobe can be configured to move substantially freely in three mutually perpendicular directions. The microprobe can be configured to translate in a first direction and rotate substantially freely in plane perpendicular to the first direction.

Embodiments can have one or more of the following features.

The first end of the microprobe can be in the fluid reservoir, and the second end of the microprobe can be capable of extending to the exterior of the housing.

The microprobe can be mechanically coupled to the flexible member.

The microprobe can be a needle or a microneedle.

The flexible member can be a septum.

The device can further include a pump in fluid communication with the fluid reservoir. The pump can be configured to draw a fluid from the microprobe into the fluid reservoir. The pump can be configured to deliver a fluid from the fluid reservoir to the microprobe. The pump can be a gas generating source. The pump can be an electrochemical cell.

The device can be a device for delivering a fluid from the fluid reservoir to the exterior of the device via the microprobe.

The device can be a device for delivering a fluid to the fluid reservoir from the exterior of the device via the microprobe.

The microprobe can be capable of moving a distance in a first direction that is at least about two percent (e.g., at least about five percent, at least about 10 percent, at least about 20 percent, at least about 30 percent, at least about 40 percent, at least about 50 percent, at least about 60 percent, at least about 70 percent, at least about 80 percent, at least about 90 percent) of a distance the microprobe is capable of moving in a second direction perpendicular to the first direction. The microprobe can be capable of moving a distance in a third direction that is at least about two percent (e.g., at least about five percent, at least about 10 percent, at least about 20 percent, at least about 30 percent, at least about 40 percent, at least about 50 percent, at least about 60 percent, at least about 70 percent, at least about 80 percent, at least about 90 percent) of the distance the microprobe is capable of moving in the second direction, the third direction being perpendicular to the first and second directions.

In another aspect, the invention features a fluid delivery device that includes a first housing and a flexible member within the interior of the first housing and mechanically coupled to the first housing. The flexible member forms first and second chambers within the interior of the first housing. The device also includes a gas generator in fluid communication with the flexible member via the first chamber of the first housing and a microprobe connected to the first housing so that when the gas generator produces a gas pressure sufficient to move the move the flexible member a portion of a fluid disposed in the second chamber is ejected via the microprobe. The device additionally includes a second housing in fluid communication with the first chamber of the first housing so that the second housing is capable of increasing the pressure in the first chamber of the first housing to increase a rate of fluid ejection via the microprobe.

In a further aspect, the invention features a fluid delivery device that includes a housing and a flexible member within the interior of the housing and mechanically coupled to the housing. The flexible member forms first and second chambers within the housing. The device also includes a microprobe connected to the housing and in fluid communication with the first chamber of the housing and a gas generator in fluid communication with the second chamber of the housing. The gas generator is capable of increasing the pressure in the second chamber to move the flexible member thereby ejecting a fluid disposed in the first chamber out of the housing via the microprobe. The device further includes a current generator in electrical communication with the gas generator. The current generator is configured so that when a current output by the current generator is varied, the gas output by the gas generator is correspondingly varied and the rate of fluid ejected by the microprobe is also correspondingly varied.

In one aspect, the invention features a fluid delivery device that includes a housing and a flexible member disposed in the interior of the housing and mechanically coupled to the housing. The flexible member forms first and second chambers within the housing. A microprobe is connected to the housing and in fluid communication with the first chamber of the housing. The device also includes a gas generator in fluid communication with the second chamber of the housing. The gas generator is capable of increasing the pressure in the second chamber to move the flexible member thereby ejecting a fluid disposed in the first chamber out of the housing via the microprobe. The device further includes at least one pressure relief valve in fluid communication with the second chamber of the housing. The pressure relief valve(s) is(are) able to compensate for a difference between a pressure of the interior of the housing and a pressure of the exterior of the housing.

In another aspect, the invention features a fluid delivery device that includes a housing and a flexible member disposed in the interior of the housing and mechanically coupled to the housing. The flexible member forms first and second chambers within the housing. A microprobe connected to the housing and in fluid communication with the first chamber of the housing, and a gas generator is in fluid communication with the second chamber of the housing. The gas generator is capable of increasing the pressure in the second chamber to move the flexible member thereby ejecting a fluid disposed in the first chamber out of the housing via the microprobe. The device also includes a second housing, a diluent reservoir in the second housing, a piston in fluid communication with the diluent reservoir and a powder chamber in fluid communication with the diluent reservoir and the first chamber of the first housing. The piston is configured so that it is capable of applying a pressure to urge a fluid from the diluent reservoir to the powder chamber, thereby mixing the fluid with a powder contained in the powder reservoir to form a mixture and to urge the mixture into the first chamber of the first housing.

In a further aspect, the invention features a sensor system that includes a microprobe, a sensor and a pump. The pump is configured to apply a suction to the microprobe so that the microprobe can withdraw a fluid from a body and pass the fluid to the sensor for detection. The sensor system can further include a flow restriction device between the microprobe and the sensor along a fluid flow path from the microprobe to the sensor and a re-fill device in fluid communication between the pump and the sensor along a fluid flow path from the pump to the sensor.

In one aspect, the invention features a fluid delivery device that includes a housing a piston in the interior of the housing, and a gas source in fluid communication with the interior of the housing. The gas source is configured to exert a pressure against the piston in a first direction. The device also includes a resilient device configured to exert a pressure against the piston in a second direction opposite the first direction, an arm, an actuation device and a valve having an open position and a closed position.

In another aspect, the invention features a device that includes a fluid reservoir capable of containing a fluid and a first drive mechanism configured to remove a predetermined amount of the fluid from the fluid reservoir when the first drive mechanism is actuated. The device is configured to prevent the first drive mechanism from being re-actuated until the predetermined amount of the fluid is removed. The device can further include a second drive mechanism configured to remove fluid from the fluid reservoir at a first predetermined rate. The first drive mechanism can enable fluid to be removed from the fluid reservoir at a second predetermined rate different than the first predetermined rate. The second predetermined rate can be higher than the first predetermined rate. The second drive mechanism can be a gas generating source. The gas generating source can be in fluid communication with a movable member. The first drive mechanism can be a compressive force. The first drive mechanism can be a spring.

In one aspect, the fluid delivery systems can be designed to provide improved flexibility and/or patient comfort. For example, the device is designed so that a rigid microprobe (e.g., a microneedle or a rigid needle) can be inserted into a subject (e.g., a human) while the device maintains several degrees of freedom so that the subject can move while feeling reduced pain because the system responds to the subject's movement.

In some embodiments, the invention features a device that includes a fluid reservoir, a septum, a rigid microprobe (e.g., a needle or a microneedle), and a housing having an orifice.

Embodiments may include one or more of the following features. The device can have several degrees of freedom of movement. The device can move relative to a subject. The septum can move, or it can be stationary. The device can include flexible tubing mechanically coupled to the rigid microprobe. The device can be a component of an electrochemical cell system.

The systems and methods can deliver a fluid to a subject with greater subject comfort, e.g., with a rigid member, and high reliability.

In another aspect, the invention features systems and methods that include delivering a fluid from a reservoir to a patient at a first rate, then delivering the fluid from the reservoir to the patient at a second rate different than the first rate.

In some embodiments, the systems and methods can provide both fluid (e.g., a pharmacological compound, such as a therapeutic agent, such as insulin) delivery to a patient (e.g., a human) at a relatively constant period of time and fluid delivery at an increased rate for a desired period of time. In certain embodiments, this can correspond to a basal delivery rate and a bolus delivery rate, respectively.

In one embodiment, the invention provides a device that includes a delivery device, an auxiliary gas source and a conduit that provides fluid communication between the delivery device and the auxiliary gas source.)

The delivery device can include a gas source, a deformable layer, a fluid reservoir and a needle or microneedle in fluid communication with the fluid reservoir. The components of the delivery device can be arranged so that as the gas source creates a gas within the delivery device the created gas exerts a pressure against the deformable layer causing the deformable layer to exert a pressure against the fluid reservoir, causing the fluid in the fluid reservoir to exit the delivery device via the needle or the microneedle.

The fluid can be a pharmacological compound (e.g., a therapeutic agent, such as insulin). The gas source in the delivery device can be an electrochemical cell (e.g., a fuel cell). The auxiliary gas source can house a gas mixture at a pressure higher than the pressure of the gas in the delivery device. The auxiliary gas source can include a gas source. The gas source in the auxiliary gas source can be an electrochemical cell (e.g., a fuel cell).

In another aspect, the invention features a device that can deliver a fluid, such as a therapeutic agent, variably, for example, by varying the current output from a current source.

In one embodiment, the invention features a device having a first chamber, a second chamber, and a deformable membrane between the first and second chambers. The second chamber includes a variable and controllable current source electrically connected to a gas generator.

In another aspect, the invention features systems and methods that compensate for a gas pressure differential between an interior and exterior gas pressure to a fluid delivery device.

Compensation can be achieved using one or more valves. For example, compensation can be achieved by having one or more valves open or close as a result of the gas pressure differential.

The systems and methods can reduce overdelivery and/or underdelivery of fluid to a subject (e.g., a human) when the gas pressure differential between the interior and exterior of the delivery device meets or exceeds some predetermined level.

The systems and methods can reduce overdelivery or underdelivery of fluid to a subject (e.g., a human) when the gas pressure external to the delivery device undergoes a relatively rapid decrease or increase, respectively (e.g., when ascending or descending, respectively, in an airplane).

In some embodiments, the invention features a device that includes a housing, a gas source, a deformable layer, a fluid reservoir, a valve, and a transmission device. The valve can be designed to provide fluid communication between the interior and exterior of the housing when the valve is in a first position, and/or to prevent fluid communication between the interior and exterior of the housing when the valve is in a different position. The device can include more than one valve.

The gas source can create a gas that exerts a force against the deformable layer to cause a fluid contained in the fluid reservoir to exit the device via the transmission device. The gas source can be an electrochemical cell, such as, for example, a fuel cell. The transmission device can be a needle or a microneedle.

In some embodiments, the invention features a device that includes a housing, a gas source, a piston, a spring, a valve, and an actuation arm.

Embodiments include one or more of the following features. The components of the device can be assembled so that the gas source can form a gas that exerts a pressure against the piston to move the piston in a direction away from the gas source. The piston and actuation arm can be mechanically coupled. The spring can be disposed within the housing so that it exerts a force in a direction opposite to the direction of the force created when the gas source forms a gas. The actuation arm can be coupled to a pumping mechanism. The actuation arm can be coupled to a deformable membrane so that the actuation arm can exert a force against the deformable membrane. The deformable membrane can be coupled to a fluid reservoir so that the deformable membrane can exert a force against a fluid contained in the fluid reservoir. The fluid reservoir can be in fluid communication with a needle or a microneedle. The actuation arm can exert a force against the deformable membrane, which can exert a force against a fluid in the fluid reservoir, and the fluid can exit the device via the needle or the microneedle.

In another aspect, the invention features a device that includes two housings, the first housing can be used to mix a diluent and a powder to form a mixture, and the second housing can be used to transfer the mixture to a subject.

Embodiments include one or more of the following features. The first housing can include a diluent chamber and a powder chamber. The diluent and powder chambers can be in fluid communication. The first and second housings can be in fluid communication via a seal, which prevents fluid communication between the first and second housings until the seal is opened or broken. The second housing can include a reservoir in fluid communication with the powder chamber via the seal. The second housing can further include a gas source and a deformable layer. The second housing can further include a transmission device so that fluid can exit the fluid reservoir via the transmission device.

In another aspect, the invention features a method that includes transferring diluent from a diluent chamber in a first housing to a powder chamber in the first housing to form a mixture, and transferring the mixture to a fluid reservoir in a different housing.

Embodiments include one or more of the following features. The method can further include transferring the mixture from the fluid reservoir to a subject via a transmission device. The methods and devices can include an electrochemical cell (e.g., a fuel cell).

In another aspect, the invention features sensors, such as, for example, pumps that can be used, for example, to detect an analyte (e.g., glucose) in a patient, as well as systems containing such sensors and methods. A device, such as an indwelling biosensor, can be used to monitor certain physiological conditions, such as, for example, the amount and/or concentration of an analyte (e.g., glucose) in a patient's blood.

In some embodiments, the invention features a system having a microprobe, a sensor and a pump. The microprobe, sensor and pump are in fluid communication.

Embodiments include one or more of the following features. The pump can be an electrochemical cell. The electrochemical cell can be capable of operating in a mode that removes oxygen from the system. The microprobe can be in fluid communication with a subject. The devices and methods can be used to withdraw, to measure and/or to detect a sample, e.g., an analyte of interest, in a subject without exposing (e.g., without directly exposing) the sensor to the subject's tissue.

In one aspect, the invention features a fluid delivery system capable of delivering a basal dosage (e.g., over about 24 hours) of a fluid, such as a drug, and/or delivering a bolus dosage of the fluid. A basal dosage can be, for example, about 0.5 to about 3 units per hour, and a bolus dosage can be, for example, a maximum of 15 units in a maximum time of 15 minutes.

In another aspect, the invention features a system and a method capable of delivering a bolus dosage accurately and reliably, for example, with minimized risk of under-dosage or over-dosage. In one embodiment, after a user starts a first cycle of bolus delivery, a dosage drive mechanism prevents the user from starting a second cycle of bolus delivery until the first cycle is completed. For example, the user is prevented from starting the second cycle mid-way through the first cycle, which can result in a one-and-a-half bolus dosage being delivered at the end of second cycle, rather than an intended one bolus dosage. The system and method ensure that the first cycle delivers the intended, predetermined dosage without unwanted interruption, thereby allowing the user to know what dosage was delivered, and minimizing the risk of under-dosage or over-dosage.

In certain embodiments, the invention features a method of sensing a fluid in a subject. The method includes creating suction in the system using an electrochemical cell to withdraw the fluid from the subject.

The devices and methods can provide sample measurement with relatively low signal loss, relatively little signal drift, and/or relatively little calibration loss. The devices and methods can provide relatively high stability (e.g., by not exposing the sensor to a tissue environment, such as a tissue environment of the subject). The systems and methods can use a pump that is relatively small, inexpensive, lightweight, compact and/or inexpensive.

Combinations of embodiments can be used.

Other features, objects, and advantages of the invention will be apparent from the description and drawings, and from the claims.

DESCRIPTION OF DRAWINGS

FIG. 9 is a cross-sectional, schematic view of an embodiment of a fluid delivery device.

FIG. 10 is a schematic diagram of a current controller.

FIG. 11 is a schematic diagram of a current controller.

DETAILED DESCRIPTION OF THE PREFERRED EMBODIMENT

The invention relates to fluid delivery and measurement systems and methods.

Figure 1:
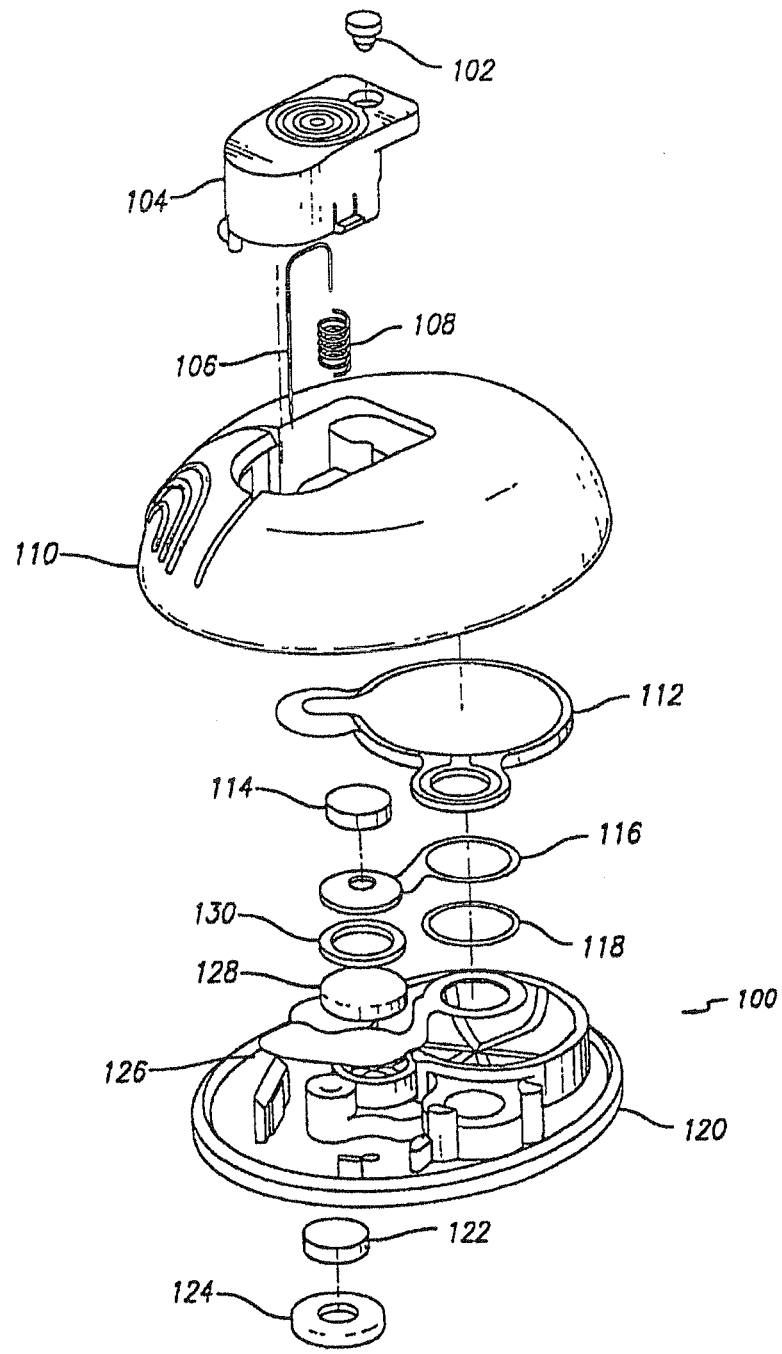
FIG. 1 is an exploded view of an embodiment of an electrochemical cell system.
Figure 2:
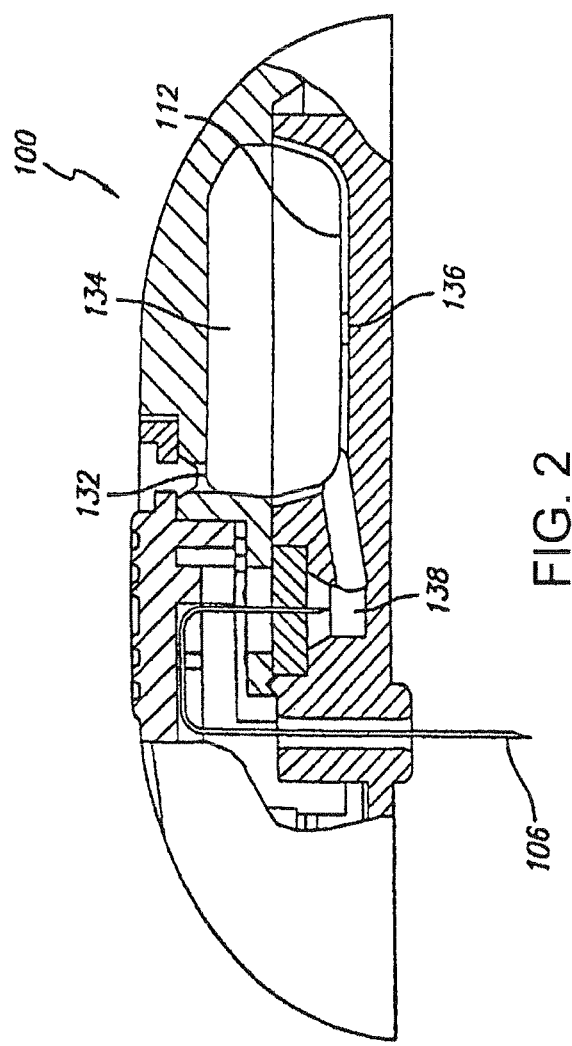
FIG. 2 is a cross-sectional view of an embodiment of an electrochemical system.

FIGS. 1 and 2 show a fluid delivery system 100 used to deliver one or more fluids such as pharmacological compounds, e.g., one or more therapeutic agents. System 100 includes a button stopper 102, a button 104, a microprobe (e.g., a needle or a microneedle) 106, a spring 108, a shell 110, a bladder 112, a delivery septum 114, a positive battery contact 116, an electrochemical cell 118, a base 120, a filling septum 122, a septum capture ring 124, a negative battery contact 126, a battery 128, a battery spacer 130, a vent 132, a drive volume 134, a fluid volume 136, and a delivery path 138. Various features and/or combinations can be incorporated into system 100 as described herein.

In some embodiments, a force is used to urge fluid from the fluid reservoir, into the microprobe and into a subject (e.g., a human). In certain embodiments, the force is created using an electrochemical cell, such as a fuel cell. Examples of electrochemical cells are disclosed, for example, in U.S. Pat. Nos. 4,402,817; 4,522,698; 4,902,278; and 4,687,423, which are hereby incorporated by reference.

Figure 3:
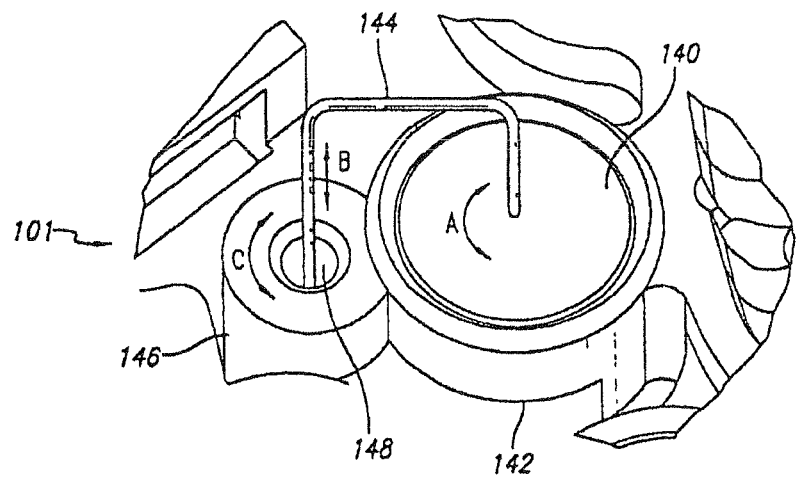
FIG. 3 is a partial perspective view of an embodiment of a fluid delivery system.

FIG. 3 shows a portion of an embodiment of fluid delivery system 101. System 101 includes a septum 140, a fluid reservoir 142 (e.g., containing a pharmacological compound), a microprobe 144 (e.g., a rigid microprobe, such as a microneedle or a rigid needle) and a housing 146 having an orifice 148. In certain embodiments, microprobe 144 can pierce septum 110 so that microprobe 144 is in fluid communication with fluid reservoir 142. Septum 140, microprobe 144, and housing 146 can move in the directions indicated by the respective bold arrows (A, B, and C), providing system 101 to have these degrees of freedom.

Figure 4:
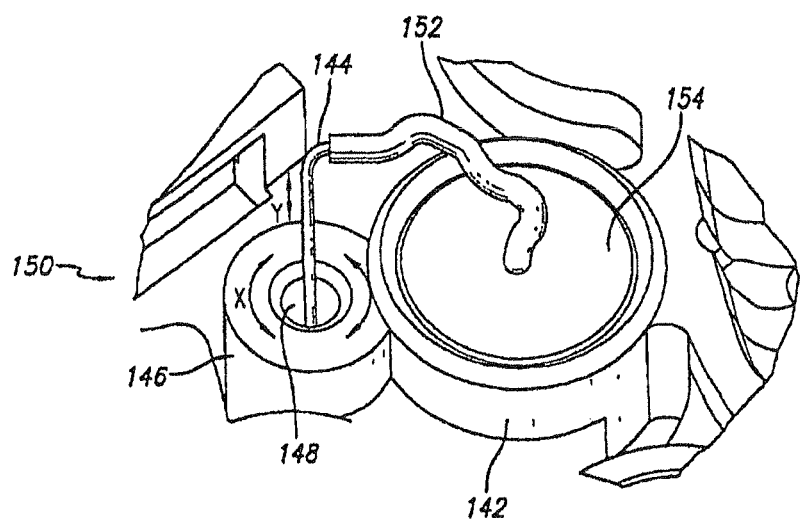
FIG. 4 is a partial perspective view of an embodiment of a fluid delivery system.

FIG. 4 shows a portion of a delivery system 150 in which a flexible portion 152 (e.g., a flexible tubing) connects microprobe 144 with a septum 154. Septum 154 is stationary, but housing 146 and microprobe 144 can move as indicated by the respective bold arrows (X and Y), providing system 150 with these degrees of freedom.

In certain embodiments, housing 146 can further include a breakable membrane, such as a polymeric membrane, extending across orifice 148. The membrane can be connected to microprobe 144 to hold the microprobe in place, e.g., centered in orifice 148, during packing and storage of system 100. When system 100 is applied to a subject, this causes microprobe 144 to move, e.g., upward, thereby pulling the membrane from orifice 148 and allowing the microprobe to move with multiple degrees of freedom.

Under certain circumstances, it can be desirable for a fluid delivery system to deliver fluid to the subject at a relatively constant rate. Under some circumstances, however, it can be desirable for the system to deliver (at least for a period of time) fluid to the subject at a relatively high rate.

Figure 5:
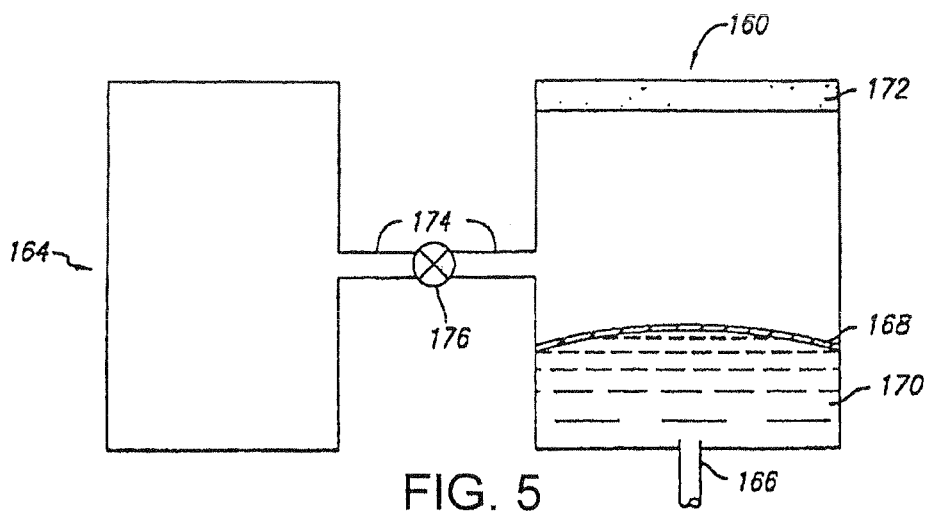
FIG. 5 is a cross-sectional view of an embodiment of a fluid delivery system.

FIG. 5 shows a system 160 including a fluid delivery device 162 and an auxiliary gas source 164. Fluid delivery device 162 includes a transport device (e.g., a microprobe or a microneedle or a needle) 166, a deformable layer (e.g., a deformable membrane) 168, a fluid reservoir (e.g., a reservoir containing pharmacological compound) 170, and a gas source 172. Fluid delivery device 162 is connected to auxiliary gas source 164 via conduit 174 that includes valve 176.

Under certain circumstances when it is desirable for delivery device 160 to deliver fluid to the subject via device 162 at a relatively constant rate, valve 176 is generally closed so that device 160 and auxiliary gas source 164 are not in fluid communication. When valve 174 is closed, fluid delivery device 162 delivers fluid from reservoir 168 to the subject via device 162 as follows. Gas source 172 forms a gas inside device 162 between gas source 172 and layer 168. As the amount of gas formed by source 172 increases, layer 168 is deformed and exerts a pressure against fluid in reservoir 170, thereby forcing the fluid through device 166. Gas source 172 can be, for example, an electrochemical cell, such as a fuel cell that generates oxygen in device 110, as described above.

Under circumstances when it is desirable to deliver (at least for a period of time) fluid to the subject via device 166 at a relatively high rate, the pressure of gas in auxiliary gas source 164 is held at and/or increased to a pressure higher than the gas pressure in device 162. Valve 176 is then opened, allowing gas to flow from source 164 into device 162 via conduit 174. This increases the pressure exerted on layer 168, thereby increasing the rate at which fluid is delivered from reservoir 170 to the subject via device 166.

Figure 6:
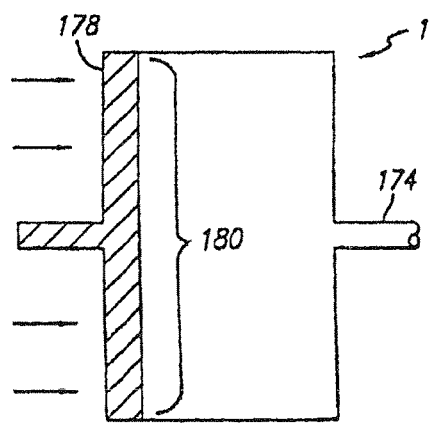
FIG. 6 is a cross-sectional view of an embodiment of an auxiliary gas source.
Figure 7:
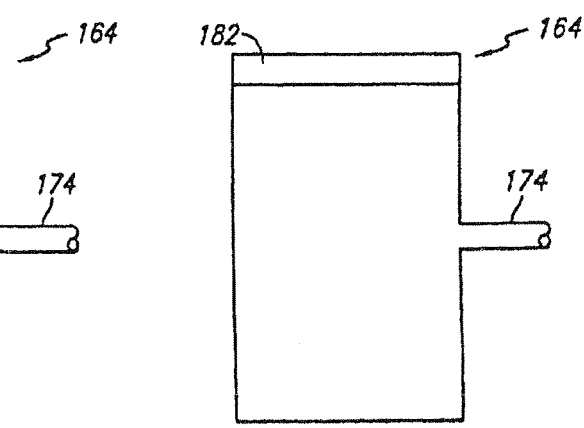
FIG. 7 is a cross-sectional view of an embodiment of an auxiliary gas source.
Figure 8:
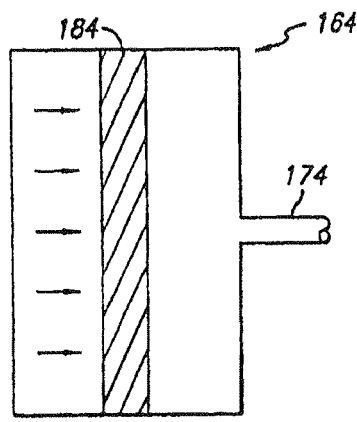
FIG. 8 is a cross-sectional view of an embodiment of an auxiliary gas source.

Auxiliary gas source 164 can be a body of gas held at a relatively high pressure. Alternatively or additionally, gas source 164 can include a piston 178 that is depressed in conjunction with the opening of valve 176 and a portion 180 that moves as piston 178 is depressed (FIG. 6). FIG. 7 shows another embodiment in which auxiliary gas source 164 includes a gas source 182 that generates a gas within the auxiliary gas source, such as described above with respect to device 162. For example, gas source 182 can be an electrochemical cell as described above. In certain embodiments, auxiliary gas source 164 can provide an increased pressure via chemical reactions (e.g., relatively rapid chemical reactions) that occur within the auxiliary gas source (e.g., reactions between vinegar and sodium bicarbonate). The gases created can be directly added into device 162, or an increased pressure can be achieved in device 162 by allowing the gases created in the chemical reactions to push, for example, a syringe plunger 184 that increases the gas in device 162 (FIG. 8).

In some embodiments, the gas pressure can be held at a relatively high value in auxiliary gas source 164. In certain embodiments, the gas pressure in auxiliary gas source 164 is increased just prior to, or at the same time as, valve 176 is opened.

Valve 176 may be manually opened as desired. Valve 176 may be opened at predetermined intervals. Valve 176 may be opened based upon the value of some parameter (e.g., the concentration of an analyte, such as glucose, in a patient).

Alternatively or in addition, in some embodiments, it is desirable for a fluid delivery system to deliver a fluid at a predetermined rate, e.g., a variable rate of delivery.

FIG. 9 shows a fluid delivery device 190 that includes a housing 192 and a deformable member (e.g., a deformable membrane) 194 inside the housing. Housing 192 and member 194 define a first chamber 196 and a second chamber 198. Device 190 includes a microprobe 199, such as a needle or a microneedle, having a lumen in fluid communication with first chamber 196 and an environment outside housing 192.

First chamber 196 includes a pharmacological compound 200, such as, e.g., insulin.

Second chamber 198 includes a button 202, a current generator 204, e.g., a DC current generator, in electrical communication with the button, and a gas generator 206 in electrical communication with the generator. Gas generator 206 is generally as described above. When a user presses button 202, this activates generator 204, which in turn sends a current to gas generator 206 to create a gas (e.g., oxygen gas) in second chamber 198. As gas is generated, pressure in second chamber 198 increases, which exerts a force on membrane 194 (e.g., pushes membrane toward microprobe 199). This, in turn, pushes compound 200 out through the lumen of microprobe 199 to, for example, a subject.

In some embodiments, the rate at which compound 200 is delivered through microprobe 199 is controlled by controlling the amount of current that generator 204 produces. This, in turn, controls the amount of gas generated by gas generator 206, the amount of pressure created in second chamber 198, and the amount of force exerted on membrane 194. For example, an increase in current output from current generator 204 increases compound delivery; and a decrease in current output decreases compound delivery.

The current from current generator 204 can be controlled or altered by using a standard current generator having a selector switch configured to alter the resistance in the circuitry of the generator. Current can be increased by switching to a low resistance resistor, and current can be decreased by switching to a high resistance resistor. FIGS. 10 and 11 show a FET and LM334 current controller, respectively, that can be used to control current by changing resistors. With these current generator systems, the active device can regulate current even with decay in the voltage of the battery.

In some embodiments, the current control generator or system can be combined with a software system, e.g., one having a microprocessor, for remote control by the user. Accordingly, a variety of configurations can be implemented depending on the clinical need of the patient and the properties of a therapeutic agent. For example, the therapeutic agent can be delivered according to a circadian schedule, such as high dosage when the patient is asleep. Thus, this system permits an "electronic formulation" or adjustment of therapeutic agent dosage or delivery over the period of ambulation in a delivery system that can, for example, be disposable.

Figure 12:
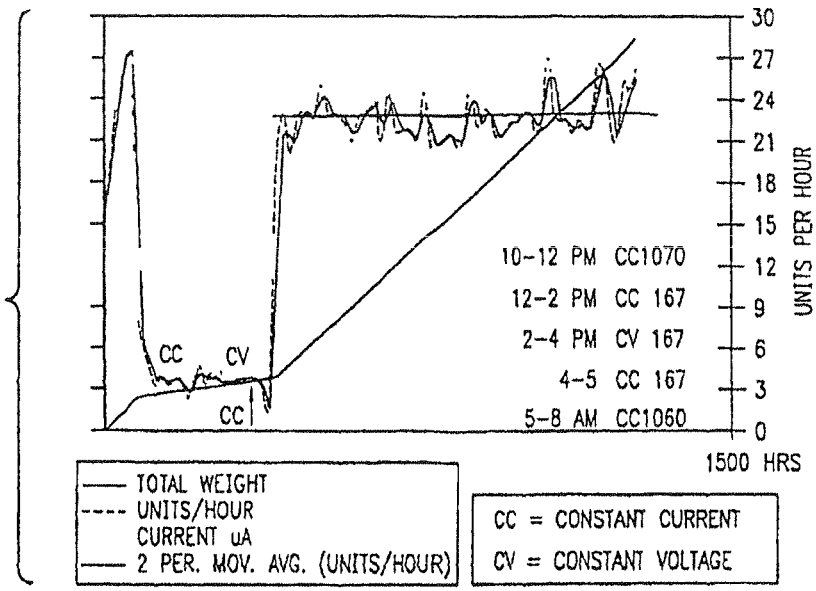
FIG. 12 is a plot of fluid delivery as a function of time.

FIG. 12 is a plot of fluid, e.g., a therapeutic agent, delivery (in units per hour) as a function of time. FIG. 12 shows that the amount of fluid delivery can be controllably varied at least over 24 hours by varying the applied current to current generator 204. For example, from 10-12 pm, a constant current (CC) of about 1,070 microamps was applied, which delivered about 30 units per hour. When the current was reduced to about 167 microamps, the rate of delivery decreased to about 3-4 units per hour. Then, the rate of delivery can be increased again by increasing the current. The current output from generator 204 can be controlled by a variety of ways, including using constant current and/or using constant voltage.

Under certain circumstances, there can be a relatively rapid change in the ambient gas pressure external to a fluid delivery system (e.g., during ascent or descent of an airplane). This can result in a change in the rate of deliver of the fluid to the subject.

Figure 13:
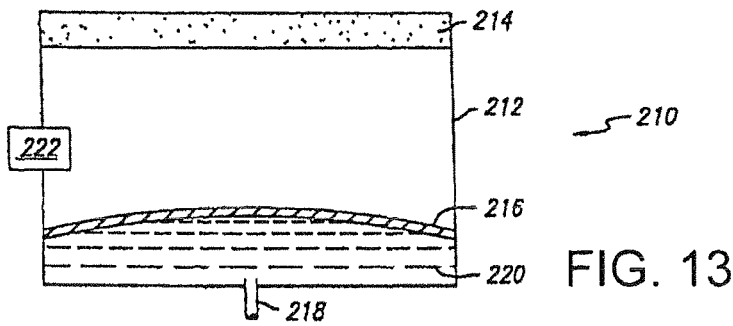
FIG. 13 is a cross-sectional view of an embodiment of a fluid delivery system.

FIG. 13 shows a fluid delivery system 210 including a housing 212, a gas source 214, a deformable layer 216, a transmission device (e.g., a microprobe, a microneedle or a needle) 218, a fluid reservoir 220 containing a fluid, and a valve 222. System 210 delivers fluid from reservoir 220 to a subject when valve 222 is closed and gas source 214 forms a gas inside housing 212 between the gas source and layer 216. As the amount of gas formed by source 214 increases, layer 216 is deformed and exerts a pressure against fluid in reservoir 220, thereby forcing the fluid through device 218. In certain embodiments, the gas pressure inside housing 212 between gas source 214 and layer 216 can be slightly higher than the ambient gas pressure external to system 210.

Without wishing to be bound by theory, it is believed that the change in delivery rate that is due to the change in the gas pressure differential between the ambient gas pressure external to system 210 and the gas pressure inside housing 212 between gas source 214 and layer 216. For example, assuming an ideal gas forms the ambient environment external to system 210 and an ideal gas forms the gas pressure inside housing 212 between gas source 214 and layer 216, a change in the ambient gas pressure from 14.7 pounds per square inch (approximate ambient gas pressure at sea level) to 10 pounds per square inch (approximate ambient gas pressure at 15,000 feet), can correspond to an almost 50% increase in the gas volume. This can result in overdelivery of the fluid from reservoir 220 to the subject. Similarly, underdelivery of the fluid from reservoir 220 to the subject can occur as the ambient gas pressure external to system 210 undergoes a relatively rapid decrease (e.g., when a plane descends).

Accordingly, valve 222 is designed to open to assist in decreasing a gas pressure differential between the ambient gas pressure external to system 210 and the gas pressure inside housing 212 between gas source 214 and layer 216. For example, valve 222 can be a bi-directional valve designed so that when this gas pressure differential meets or exceeds some predetermined value the valve allows gas to flow from the relatively high gas pressure environment to the relatively low gas pressure environment, thereby assisting in decreasing the gas pressure differential. Such valves are commercially available from, for example, Vernay.

Figure 14:
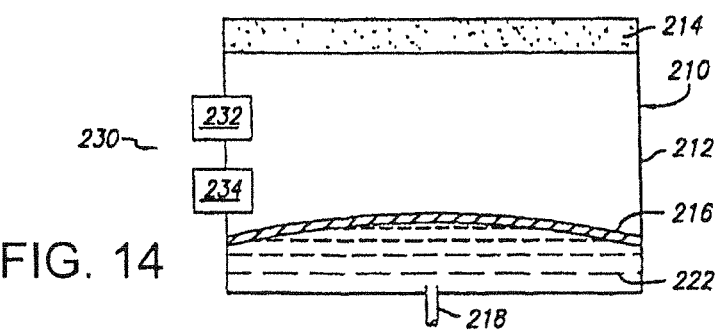
FIG. 14 is a cross-sectional view of an embodiment of an auxiliary gas source.

FIG. 14 shows a fluid delivery system 230 that contains valves 232 and 234, each of which is a one-way valve (e.g., a "pop-off" valve, a "mushroom-capped" valve). Valves 232 and 234 are designed so that, if the ambient external gas pressure to system 210 exceeds the gas pressure inside housing 212 between gas source 214 and layer 216 by some predetermined value, valve 232 opens so that the gas pressure differential decreases. Valves 232 and 234 are also designed so that, if the gas pressure inside housing 212 between gas source 214 and layer 216 exceeds the ambient external gas pressure to system 210 by some predetermined value, valve 234 opens so that the gas pressure differential decreases.

Various combinations of pressure relief valves can be used. Generally, the combination(s) of relief valve(s) is designed to reduce the gas pressure differential between the internal and external gas pressures of the delivery system when the gas pressure differential meets or exceeds some predetermined value.

In certain embodiments, the internal pressure differential at which the device works to provide a desired fluid flow can be relatively low (e.g., about 0.2 PSIG or less). In some embodiments, one or more components can be included in the device to provide a resistive force to increase the internal pressure differential at which the device works to provide the desired fluid flow. For example, a spring can be disposed beneath the flexible member. This can, for example, decrease the absolute and/or relative pressure differential used for pressure relief valve(s) to operate relative the internal pressure differential used to provide desired fluid flow for the device, thereby enhancing the overall sensitivity of the device to changes in the internal/external pressure differential (e.g., due to a change in altitude).

Figure 15:
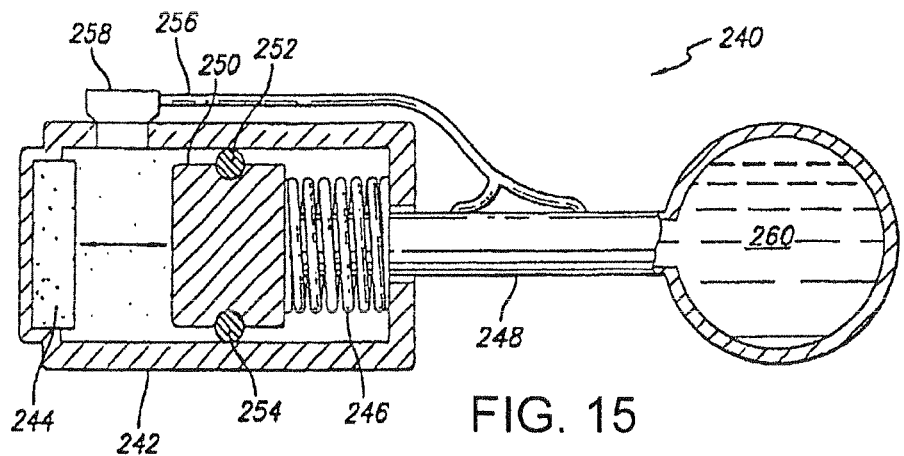
FIG. 15 is a cross-sectional view of an embodiment of a fluid delivery system.

Other embodiments for minimizing overdelivery and/or underdelivery are possible. FIG. 15 shows a fluid delivery system 240 including a housing 242, a gas source 244, a resilient device 246 (e.g., a spring), an arm 248 (e.g., a drive arm, a cam, a linkage, a ratchet device), a piston 250, seals 252 and 254 (e.g., O-rings), an actuation device 256 (e.g., a valve actuation arm), and a valve 258. Arm 248 is in mechanically coupled to a pumping mechanism 260 (e.g., a deformable layer) that delivers a fluid to a patient via a transmission device, such as a microprobe, a microneedle or a needle.

When valve 258 is closed, gas source 244 forms a gas, which urges piston 250 against device 246 and which moves arm 248 away from source 244. When the piston reaches a position at a predetermined distance from gas source 244, device 256 causes valve 258 to open, decreasing the gas pressure differential between the interior of housing 242 and the exterior of the housing. Alternatively, the position of valve 258 (e.g., open or closed) can be selected manually, or can be determined based upon some measured parameter (e.g., the differential between the gas pressure inside housing 242 and the gas pressure outside the housing).

The rate at which piston 250 moves distally from gas source 244 can depend upon the differential between the gas pressure inside housing 242 and the gas pressure outside the housing. For example, the amount of time it takes for piston 250 to move a given distance away from gas source 244 can vary proportionally with the variation in the differential in the gas pressure inside housing 242 and the gas pressure outside the housing (e.g., if at a given gas pressure differential it takes piston 250 one second to move a given distance from gas source 244, then at half that gas pressure differential, it will take piston twice as long to move that distance from the gas source).

In some embodiments, the piston and seals assembly can be replaced with a bellows sealed to the gas source. In certain embodiments, the circuitry of the gas source can be connected to flip/flop polarity so that it switches, for example, from oxygen generation mode to oxygen removal mode. The polarity can be reversed by, for example, a timed response, a mechanical limit switch, or both. In these embodiments, the system can be designed to not include the return spring or valve actuation arm, and the valve could be replaced with valves described above.

Figure 20:
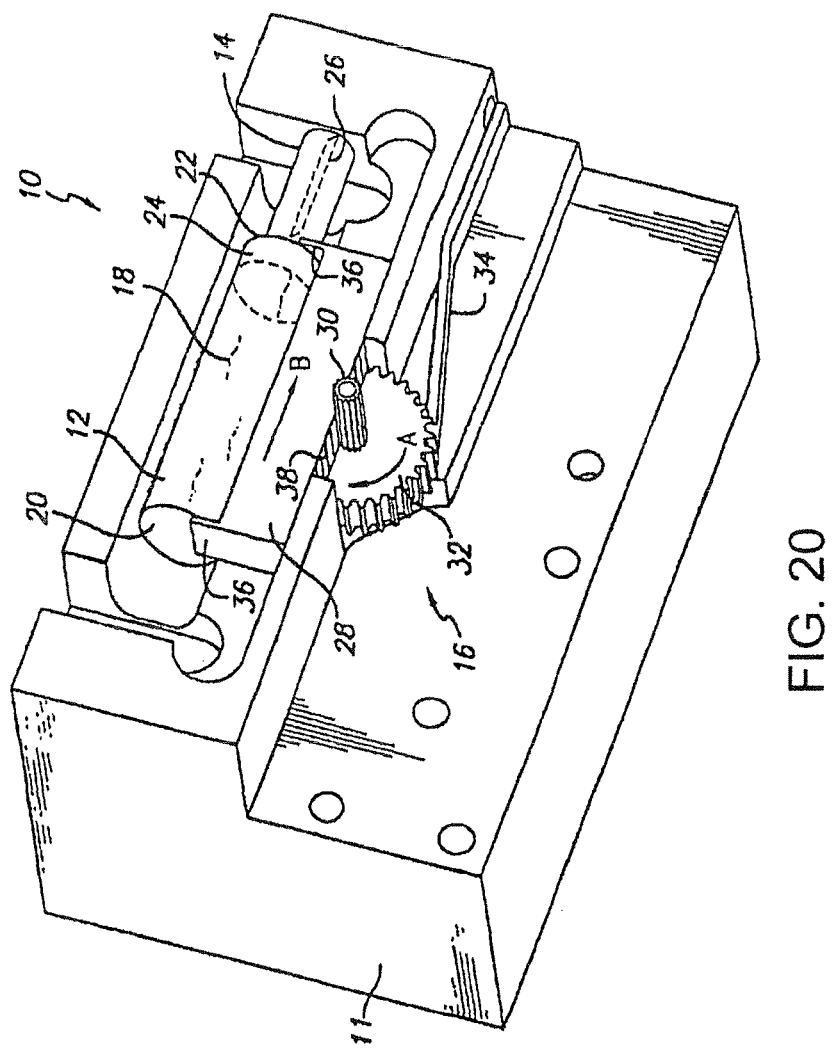
FIG. 20 is a partial, schematic diagram of an embodiment of a fluid delivery system.

Referring to FIG. 20, a fluid delivery system 10 includes base 11 positioned thereon, a fluid housing 12, a needle or microneedle housing 14, and a movement system 16 for moving the fluid housing. Fluid housing 12, e.g., a glass cylinder vial, contains a fluid 18 (e.g., a pharmacological compound, such as a drug) between a sealed end 20 and an open end 22 sealed with a pierceable member 24, such as a rubber stopper or septum. Member 24 provides fluid housing 12 with a fluid-tight seal so that fluid 18 does not leak from the housing, but member 24 and housing 14 can slide within the housing. That is, fluid housing 12 is configured to slidably receive member 24 and housing 14, as described below. Housing 14, which includes a double-pointed needle 26, is fixedly attached to base 11. Examples of housings, including a needle or a microneedle, are described herein.

Movement system 16 includes a gear rack 28, a pinion gear 30, a spur gear 32, and a pawl 34. Gear rack 28 has two projections 36 that engage, e.g., hold, ends 20 and 22 of fluid housing 12 to couple the fluid housing to the gear rack. Gear rack 28 further includes teeth 38 that engage pinion gear 30, and the pinion gear is rotatably connected to spur gear 32. The gear ratios of gear rack 28, pinion gear 30 and spur gear 32 are selected to provide a predetermined amount of movement of the gear rack in response to a predetermined movement of the spur gear, e.g., sufficient for drug delivery. Pawl 34 is attached to base 11 at one end and engages with the teeth of spur gear 32 at the other end. Pawl 34 serves as an anti-reverse mechanism that allows spur gear 32 to rotate in only one direction, here clockwise (arrow A). Pawl 34 also maintains a load on fluid housing 12 as a drive mechanism (describe below) is reset.

During use, fluid 18 is delivered from fluid housing 12 through needle or microneedle 26 by translating fluid housing 12 toward housing 14 (arrow B). Spur gear 32 is rotated clockwise, which rotates pinion gear 30 clockwise. Pawl 34 prevents spur gear 32 from rotating counter-clockwise. As pinion gear 30 rotates, its teeth engage with teeth 38 of gear rack 28, which translates the gear rack in the direction of arrow B. Since gear rack 28 is coupled to fluid housing 12 by projections 36, the fluid housing is also translated in the direct of arrow B toward housing 14. As fluid housing 12 is moved toward housing 14, one end of needle or microneedle 26 pierces through member 24, and the other end of the needle or microneedle pierces a subject, e.g., a human. Fluid 18 is delivered through needle or microneedle 26 by continuing to move fluid housing 12 toward housing 14 with member 24 sliding inside the fluid housing, e.g., like a piston. In some embodiments, it is preferable that needle or microneedle 26 pierces member 24, and fluid 18, e.g., a drop or less, flows entirely through the needle or the microneedle before the needle or the microneedle pierces the subject. This can prevent or minimize contamination of fluid 18, e.g., if the needle or the microneedle pierces the subject first and the subject's bodily fluid can enter fluid housing 12.

Figure 21:
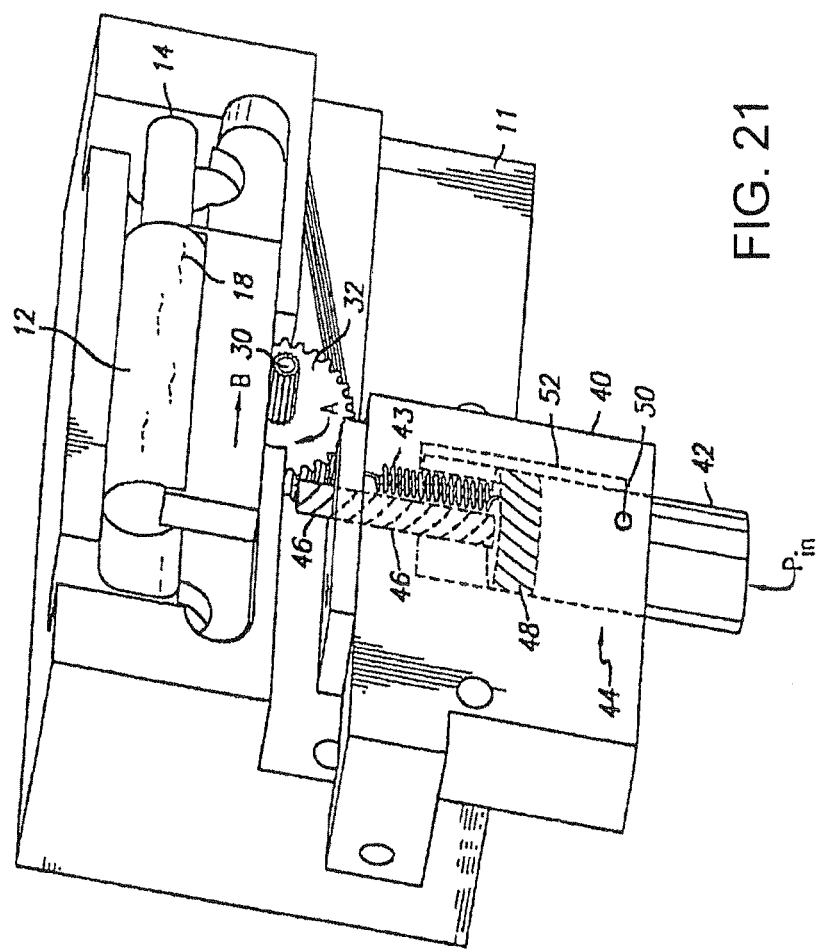
FIG. 21 is a partial, schematic diagram of an embodiment of a fluid delivery system.

FIG. 21 shows an embodiment of fluid delivery system 10 having a drive mechanism 40 capable of delivering a basal dosage of fluid 18. Mechanism 40 includes an inlet port 42, a piston system 44, and a driver 46. Port 42 is interfaced with a gas-generating source (not shown) such as an electrochemical cell, e.g., an electrolytic cell. Gas-generating sources are disclosed in U.S. Pat. Nos. 4,402,817; 4,522, 698; 4,902,278; and 4,687,423. Gas from the gas source is provided to drive piston system 44, which includes a piston 48 and an exhaust port 50. Piston 48 s connected to a torsion spring 49 configured to force the piston toward inlet port 42. Piston 48 is also connected to driver 46 and linked to exhaust port 50, e.g., by a valve, by a linkage 52. Driver 46 is configured to engage with spur gear 32 such that as piston 48 moves away from inlet port 42, the driver can rotate the spur gear, e.g., clockwise. Linkage 52 is provided to open exhaust port 50 when piston 48 reaches a predetermined position along its upstroke, e.g., at the end of its stroke, and triggers the linkage. Opening exhaust port 50 vents gas in piston system 44 so that spring 49 can force piston 48 back to an initial stroke position, e.g., adjacent to port 42. After gas is vented from piston system 44 and piston 48 completes its downstroke, linkage 52 closes exhaust port 50.

During use, gas is continuously introduced via port 42 into piston system 44. With piston 48 at the initial stroke position and port 50 closed, as the gas pressure increases in system 44 and overcomes the force of spring 49, the gas advances the piston and driver 46 toward spur gear 32, thereby rotating the spur gear. As described above, rotation of spur gear 32 delivers fluid 18 through needle or microneedle 26. Piston 48 continues to advance until it reaches a predetermined position where it causes linkage 52 to open exhaust port 50. Opening port 50 vents gas in system 44, and allows spring 49 to force piston 48 to its initial stroke position (and retracts driver 46), where linkage 52 now closes the exhaust port. Since gas is continuously introduced into piston system 44, the stroke cycle of piston 48 and driver 46 is repeated, thereby continuing to deliver fluid 18 through needle or microneedle 26.

Figure 22:
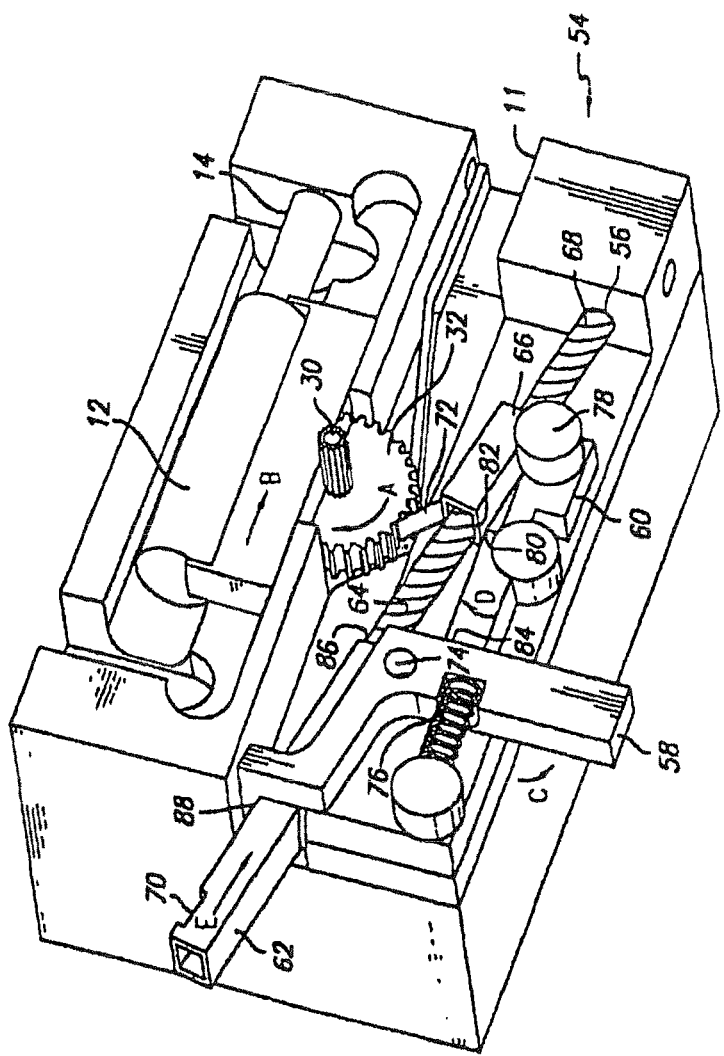
FIG. 22 is a partial, schematic diagram of an embodiment of a fluid delivery system.

FIG. 22 shows an embodiment of fluid delivery system 10 having a drive mechanism 54 capable of delivering a bolus dosage of fluid 18. Mechanism 54 is shown in an untriggered condition. Mechanism 54 includes a shaft 56, a button release lever 58, and a button lock-up bar 60.

Shaft 56 includes positioned thereon a button 62, a button extension spring 64, a bolus actuator 66, and a bolus drive spring 68. Button 62 and actuator 66 are slidably positioned on shaft 56. Button 62 is a square, hollow member having a notch 70. Springs 64 and 68 are positioned on shaft 56 such that they can be compressed and extended on the shaft when button 62 and actuator 66 are moved along the shaft. Actuator 66 is also a square, hollow member that includes an actuator tab 72, e.g., spring steel, that can engage with the teeth of spur gear 32 to rotate the spur gear, e.g., drive the gear in the direction of arrow A. Shaft 56 is connected to base 11 on one end.

Button release lever 58 is pivotally connected to base 11 at connection 74. Lever 58 is biased in the direction of arrow C by a lever spring 76. Lever includes a portion 88 that can engage with notch 70.

Button lock-up bar 60 is also pivotally connected to base 11, at connection 78. Button lock-up bar 60 is biased in the direction of arrow D by a spring (not shown). Button lock-up bar 60 includes an edge 80 that is chamfered, e.g., at about 45°, and that contacts an end 82 of bolus actuator 66 when mechanism 54 is in an untriggered condition. Lock-up bar 60 further includes an end 84 that can engage with an end 86 of button 62.

As shown in FIG. 22, in an untriggered condition, button release lever 58 is spring-biased in the direction of arrow C, and button lock-up bar 60 is spring-biased in the direction of arrow D. Springs 64 and 68 are extended.

During use, for example, when a user wants to deliver a bolus dose of fluid 18, the user first depresses button 62 (shown extended in FIG. 22) in the direction of arrow E along shaft 56 until notch 70 engages with portion 88 of button release lever 58. Portion 88 locks button 62 in a depressed position. Depressing button 62 also compresses springs 64 and 68 along shaft 56 and moves bolus actuator 66 and tab 72 in the direction of arrow E. Tab 72 deflects as it travels over the teeth of spur gear 32. Since lock-up bar 60 is biased in the direction of arrow D, and bolus actuator 66 has been moved out of contact with edge 80 by depressing button 62, the lock-up bar rotates (arrow D) about connection 78, and end 84 rotates to contact the side of the button. With button 62 depressed and locked, drive mechanism 54 is in a "cocked" condition.

To trigger drive mechanism 54, the user rotates button release lever 58 about connection 74 in the direction opposite arrow C, here clockwise. This releases the locking engagement between notch 70 and portion 88, and allows button 62 to be returned to its untriggered position by the spring force of spring 64. Similarly, bolus actuator 66 is returned to its untriggered position by the controlled and predetermined spring force of spring 68. As bolus actuator 66 returns (in the direction opposite arrow E) actuator tab 72 engages spur gear 32 at a controlled force and rotates the spur gear, thereby delivering a bolus dose at a controlled rate. When bolus actuator 66 returns to its untriggered position, edge 82 contacts edge 80 to rotate lock-up bar 60 in the direction opposite arrow D, thereby moving end 84 away from end 86 and allowing button 62 to be depressed.

Before bolus actuator 66 is returned to its untriggered position, however, lock-up bar 60 is biased in the direction of arrow D (upwardly as shown in FIG. 22); such that, if the user tried to depress button 62, end 84 would butt against end 86 and prevent the button from being depressed. This mechanism prevents the user from re-cocking and re-triggering the bolus delivery mechanism before the bolus dosage is completed. As a result, the risk that a user can deliver an unwanted bolus dosage—over-dosage or under-dosage—is minimized. Each trigger of drive mechanism 54 can provide a predetermined bolus dosage at a controlled rate, so the risk of under-dosage is minimized. The user is prevented from re-triggering the drive mechanism until the predetermined dosage is delivered, so the risk of over-dosage is minimized.

While drive mechanisms 40 and 54 are described above separately, in certain embodiments, the drive mechanisms are integrated in a fluid delivery system such that the delivery system can deliver a basal dosage and a bolus dosage on demand.

Figure 23:
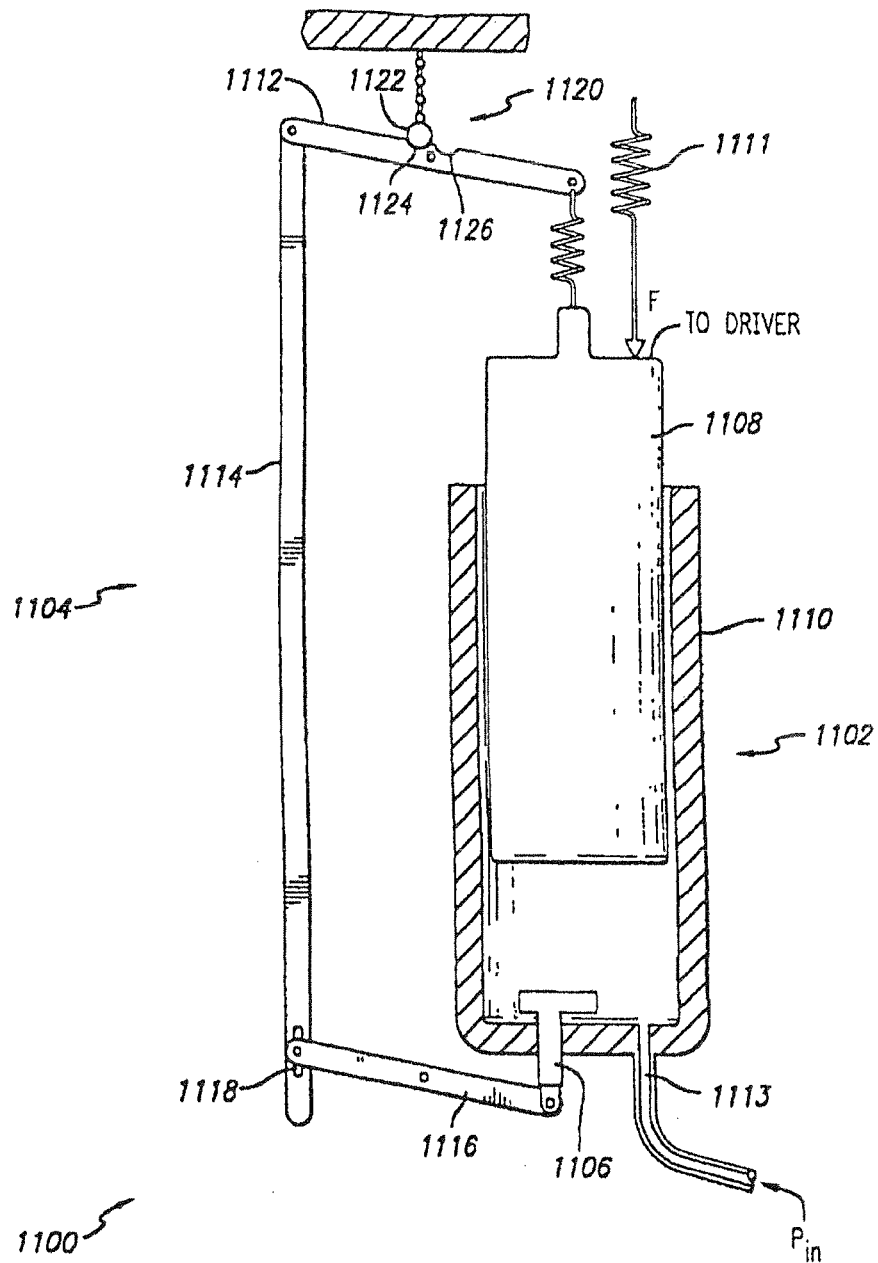
FIG. 23 is a partial, schematic diagram of an embodiment of a fluid delivery system.

While certain embodiments have been disclosed, the invention is not limited in this sense. For example, FIG. 23 shows an embodiment of a piston system 1100 that can be used in drive mechanism 40 described above. System 1100 includes a piston assembly 1102, a linkage assembly 1104, and a valve 1106, e.g., a T-shape valve. Piston assembly 1102 includes a piston 1108, a piston housing 1110, and a spring 1111. Spring 1111 is configured to bias piston 1108, e.g., with linear force, in the direction of arrow F, for example, to bias the piston to a position adjacent to valve 1106. In some embodiments, piston 1108 is connected to driver 46 in the drive mechanism described above to delivery fluid 18. Piston assembly 1102 further includes a gas inlet 1113 that is in fluid communication with the interior of housing 1110 and a gas source (not shown), such as an electrochemical cell described above.

Linkage assembly 1104 includes a first lever arm 1112, a linkage bar 1114, and a second lever arm 1116. First lever arm 1112 is connected to linkage bar 1114 by a freely pivoting connection; and the linkage bar is connected to second lever arm 1116 by a slotted connection 1118 and to valve 1106. First lever arm 1112 is further engaged to a ball plunger 1120 via a first detent 1124 or a second detent 1126 on the first lever arm. At one end, ball plunger 1120 includes a ball 1122 that can rest in first detent 1124 or second detent 1126. At the other end, plunger 1120 is fixedly connected, for example, to a housing of system 1100 via a spring or a rigid connection. Linkage assembly 1104 is connected to piston 1108 at one end of first lever arm 1112, for example, by a spring or a rigid connection such as a rod.

In operation, piston 1108 is at an initial position, e.g., adjacent to valve 1106. Linkage assembly 1104 is configured such that the pivoting and lever action of lever arms 1112 and 1116 and linkage bar 1114 causes the valve to be closed. Piston housing 1110 is sealed. Ball 1122 is at rest in first detent 1124.

As gas is continuously introduced via inlet 1113 into housing 1110, the gas pressure inside the housing 1110 increases and overcomes the spring force of spring 1111. Piston 1108 is moved away from valve 1106. The movement of piston 1108 can be used to drive driver 46 to deliver a fluid.

When piston 1108 reaches a predetermined position, e.g., at the end of its upstroke, the piston pushes on first lever arm 1112 such that ball 1122 is displaced from first detent 1124 to second detent 1126. This action causes linkage assembly 104 (by pivoting and lever action) to open valve 1106.

Opening valve 1106 vents gas from piston housing 1110, and the spring force of spring 1111 causes piston 1108 to return to its initial position. As piston 1108 travels back to its initial position, ball 1122 is still in second detent 1126, thereby ensuring that valve 1106 stays open until the piston returns to a predetermined position, e.g., its initial position, i.e., for the entire return stroke. For example, if valve 1106 were just "cracked" or closed during the return downstroke, piston 1108 could be stalled midway through the entire stroke cycle. When piston 1108 reaches its initial position, the piston pushes and closes valve 1106, and the mechanical action of linkage assembly 1104 displaces ball 1122 from second detent 1126 to first detent 1124. The stroke cycle of the piston is repeated as gas is introduced into housing 1110.

Thus, system 1100 is generally configured to ensure that piston 1108 completes its stroke cycle, e.g., from an initial position to a final position and back to the initial position, without restarting its cycle during the cycle. When coupled, for example, to a fluid delivery system, system 1100 can provide an accurate and reliable drive mechanism.

Figure 16:
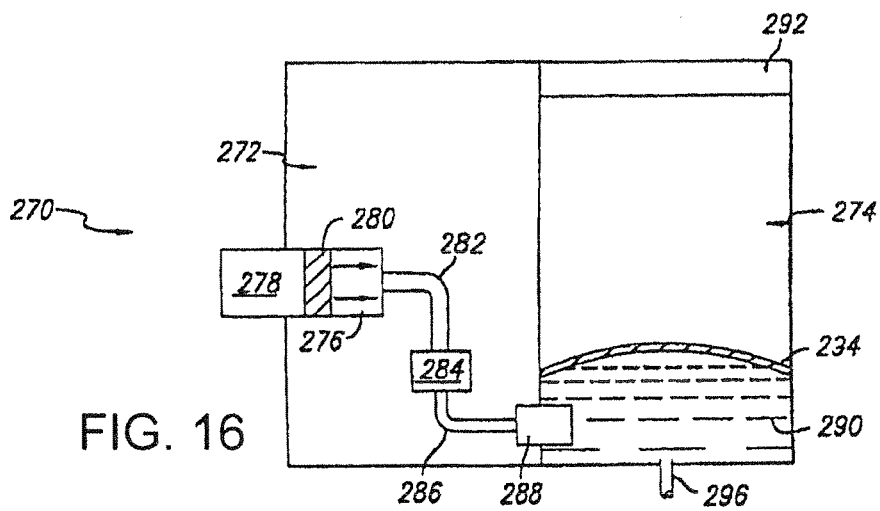
FIG. 16 is a cross-sectional view of an embodiment of a fluid delivery device.

FIG. 16 shows a system 270 that includes a first chamber 272 and a second chamber 274. Chamber 272 contains a diluent reservoir 276 coupled to a button 278 via a piston 280 so that when the button is depressed, the piston moves in the direction shown by the arrows. This causes the diluent to move along a path 282 and enter a powder chamber 284, which contains a dried powder, such as, for example, a pharmacological compound (e.g., a lyophilized therapeutic agent). When the diluent enters chamber 284, the dried powder is reconstituted. The reconstituted mixture (e.g., therapeutic agent/diluent mixture) can move along a path 286 to a seal 288. Seal 288 can be, for example, a sterility seal. If seal 288 is broken (e.g., by being sheared as system 270 is mounted on, for example, a subject), then the reconstituted mixture can pass into a reservoir 290 contained in chamber 274. Chamber 274 also includes a gas source 292 as described above, a deformable layer 294, and a transmission device 296 (e.g., a needle or a microneedle).

When gas source 292 is activated (e.g., by the user pressing a button), the gas source creates a gas in housing 274 between the gas source and deformable layer 294. This exerts a force on deformable layer 294, which, in turn, causes fluid (e.g., a fluid and the therapeutic agent/diluent mixture) in reservoir 290 to exit housing 274 via device 296. In some embodiments, the fluid is transferred into a subject (e.g., a human) (e.g., when device 296 is inserted into the subject).

In certain embodiments, the user can press a button that activates (e.g., simultaneously activates) both the electrochemical cell and causes the transmission device to be inserted into the subject so that a fluid path is connected between the fluid reservoir and the subject. In some embodiments, such as when it is desirable to have a long stroke on the button, the actions can be performed sequentially using detents or partial mechanical stops during travel of the button.

In some embodiments, a fluid delivery system can be adapted for use as a sensor.

Figure 17:
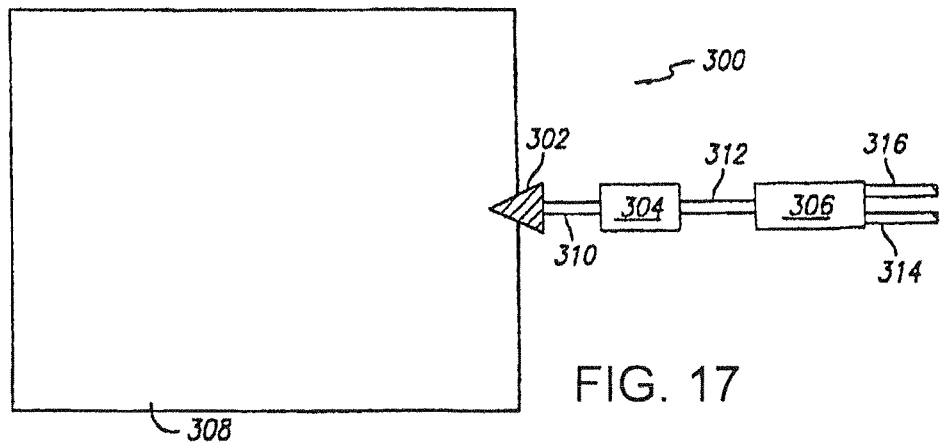
FIG. 17 is a schematic representation of an embodiment of a sensor system.

FIG. 17 shows an embodiment of a sensor system 300 including a microprobe 302, a sensor 304, a pump 306 and a subject (e.g., a human) 308. Microprobe 302 is in fluid communication with sensor 304 via a fluid path (e.g., tubing) 310, and the sensor is in fluid communication with pump 306 via a fluid path (e.g., tubing) 312.

During use of system 300, pump 306 creates a suction or partial vacuum that can remove a sample (e.g., a fluid sample, such as a blood sample) from subject 308. The sample passes through microprobe 302 (e.g., a needle or a microneedle) and along path 310 to sensor 304 (e.g., a blood glucose sensor), where one or more species of interest (e.g., analytes of interest, such as glucose) is measured. The sample then moves along path 312 to pump 306 and exits system 300 via an exhaust 314 (e.g., a gas exhaust) and/or exhaust 316 (e.g., a waste exhaust). Exhaust 314 and/or 316 can be in fluid communication with, for example, a disposable bag.

In some embodiments, pump 306 is an electrochemical cell that operates in reverse mode so that it removes oxygen present between microprobe 302 and sensor 304 (e.g., in microprobe 302, path 310, the sensor, path 312 and/or the pump) and exhausts via exhaust 314. By using up this oxygen, pump 306 reduces the pressure between microprobe 302 and sensor 304, thereby creating suction or a partial vacuum and allowing the sample to be removed from subject 308. Because there is only about 20% oxygen in air, the suction created by the electrochemical cell can be limited. An example of an electrochemical cell is a symmetrical Pt/NAFION® fuel cell. Examples of electrochemical cells are described above.

Figure 18:
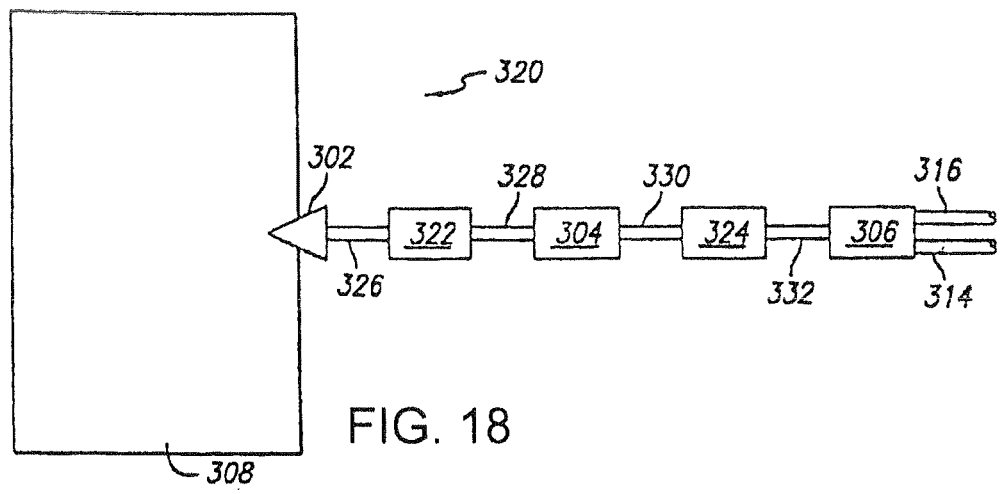
FIG. 18 is a schematic representation of an embodiment of a sensor system.

FIG. 18 shows an embodiment of a sensor system 320 that includes a flow restriction device (e.g., a valve clamp) 322 and a re-fill device (e.g., a re-fill valve) 324.

During use of system 320, pump 306 creates a suction or partial vacuum that can remove a sample (e.g., a fluid sample, such as a blood sample) from subject 308. The sample passes through microprobe 302 and along a path 326 (e.g., tubing) to flow restriction device 322. The sample then passes along a path 328 (e.g., tubing) to sensor 304. The sample then passes along a path 330 (e.g., tubing) to re-fill device 324. The sample then passes along a path (e.g., tubing) 332 to pump 306, and then out of system 320 via exhaust 314 and/or 316.

Device 324 can be used to periodically (e.g., at predetermined and/or timed intervals, and/or at intervals determined in response to a signal, such as a measurement of the amount of oxygen in fluid communication with path 330, path 332 and/or device 324) re-fill air into system 320, thereby allowing continuous or semi-continuous extraction of fluid from subject 308 via microprobe 302. When device 324 is opened to re-fill air into system 320, device 322 can be closed to prevent fluid communication between subject 304 and sensor 304.

Figure 19A:
FIGS. 19A, 19B, and 19C are graphical representations of the performance of an embodiment of a sensor.
Figure 19B:
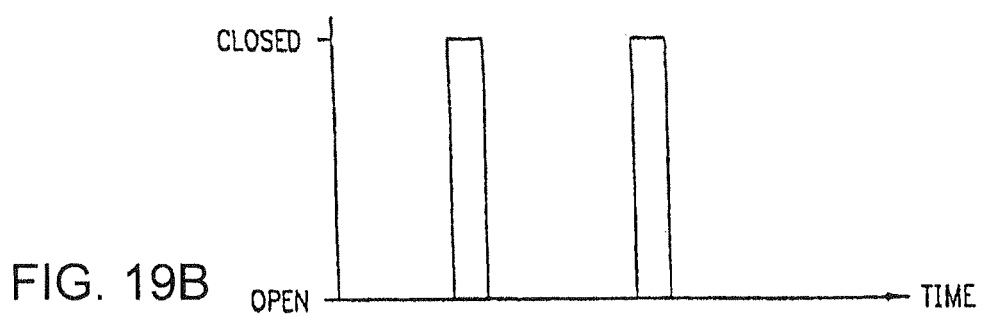
Figure 19C:
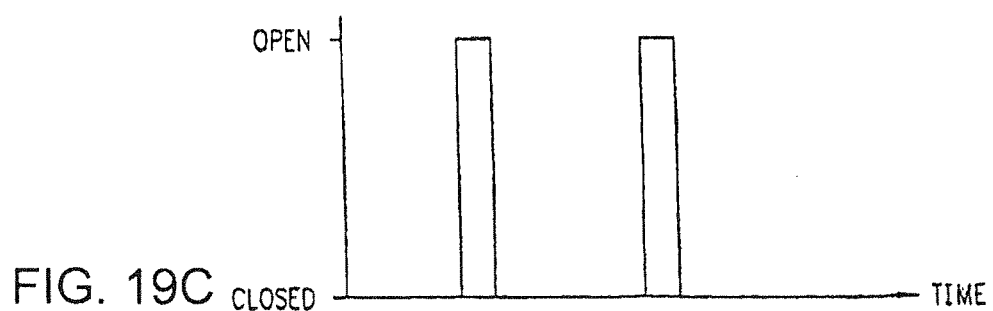

FIG. 19A shows an embodiment of oxygen values as a function of time for system 320. FIGS. 19B and 19C show the corresponding values of the position (i.e., open/closed) of devices 322 and 324, respectively, as a function of time for system 320.

In other embodiments, more than one electrochemical cell can be used to provide suction in an alternating pattern to provide continuous or semi-continuous extraction of fluid from subject 308.

Pump 306 can be placed in various positions so long as it is capable of forming suction or a partial vacuum as discussed above. For example, in some embodiments, pump 306 is between microprobe 302 and sensor 304.

Combinations of embodiments can be used.

Therapeutic agents that can be used in the devices and methods described herein include, for example, vaccines, chemotherapy agents, pain relief agents, dialysis-related agents, blood thinning agents, and compounds (e.g., monoclonal compounds) that can be targeted to carry compounds that can kill cancer cells. Examples of such agents include, insulin, heparin, morphine, interferon, EPO, vaccines towards tumors, and vaccines towards infectious diseases.

The device can be used to deliver a therapeutic agent to any primate, including human and non-human primates. The device can be used to deliver an agent, e.g., a therapeutic agent to an animal, e.g., a farm animal (such as a horse, cow, sheep, goat, or pig), to a laboratory animal (such as a mouse, rat, guinea pig or other rodent), or to a domesticated animal (such as a dog or cat). The animal to which the therapeutic agent is being delivered can have any ailment (e.g., cancer or diabetes). It is expected that the device may be most useful in treating chronic conditions. However, the device can also be used to deliver a therapeutic agent (such as a vaccine) to an animal that is not suffering from an ailment (or that is suffering from an ailment unrelated to that associated with the therapeutic agent). That is, the device can be used to deliver therapeutic agents prophylactically.

The devices and methods of the invention can be used to individually tailor the dosage of a therapeutic agent to a patient.

The devices and methods of the invention can allow for outpatient treatment with increased convenience, such as, for example, without the use of an I.V.

Devices and methods described herein can be advantageous because they can be used to promote maintenance of the concentration of a therapeutic agent in a patient's plasma within a safe and effective range. Moreover, the device can release therapeutic agents in response to the concentration of an analyte in the patient's system. Thus, the rate of drug delivery can be appropriate for the patient's physiological state as it changes, e.g., from moment to moment.

Other embodiments are within the claims.

We claim:

1. A fluid delivery device, comprising:
   a housing;
   a fluid reservoir within the housing and having a pierceable member;
   a needle having a first end and a second end and at least one bend between the first end and the second end;
   an initial position defined by the first end being fluidly disengaged from the fluid reservoir; and
   an engaged position defined by the first end extending through the pierceable member and into the fluid reservoir and the second end extending out of the housing,
   wherein the needle is configured to translate in a first direction relative to the housing between the initial position and the engaged position, and
   wherein the housing is configured to move relative to the needle in a second direction different than the first direction while in the engaged position.

2. The fluid delivery device of claim 1, wherein the needle includes a first end portion proximate the first end and a second end portion proximate the second end and a middle portion extending between and generally perpendicular to the first end portion and the second end portion, the first end portion being generally parallel to the second end portion and the first end portion having a length that is smaller than a length of the second end portion.

3. The fluid delivery device of claim 2, wherein housing is configured to rotate in the second direction while in the engaged position, and wherein the housing is configured to rotate about the first end portion while in the engaged position.

4. The fluid delivery device of claim 3, wherein the housing is configured to further rotate about the second end portion of the needle while in the engaged position.

5. The fluid delivery device of claim 2, wherein the housing is configured to rotate about the second end portion in the engaged position.

6. The fluid delivery device of claim 1, wherein the first and second ends of the needle are configured to be entirely shrouded by the housing and disengaged from the fluid reservoir in the initial position and fluidly coupled with the fluid reservoir and extending from the housing respectively when in the engaged position.

7. The fluid delivery device of claim 1, wherein the pierceable member is generally parallel to a bottom surface of the housing from which the needle extends while in the engaged position.

8. The fluid delivery device of claim 1, wherein the needle is a microneedle.

9. The fluid delivery device of claim 1, wherein the first and second ends of the needle are beveled.

10. The fluid delivery device of claim 1, wherein the pierceable member comprises a septum.

11. The fluid delivery device of claim 1, wherein the housing is configured to be adhered to a skin surface in the engaged position.

12. The fluid delivery device of claim 1, wherein the first end of the needle is configured to pierce the pierceable member in a direction substantially equal to a direction the second end of the needle extends out of the housing while in the engaged position.

13. The fluid delivery device of claim 1, wherein the housing is configured to rotate about first and second portions of the needle while in the engaged position.

14. The fluid delivery device of claim 1 further comprising:

a needle button coupling the needle and the housing.

15. The fluid delivery device of claim 1, wherein the at least one bend is approximately 90 degrees.

16. The fluid delivery device of claim 1, wherein the at least one bend includes two bends each being approximately 90 degrees.

* * * * *